US00PP28753P2

(12) United States Plant Patent
Dong

(10) Patent No.: US PP28,753 P2
(45) Date of Patent: Dec. 12, 2017

(54) KIWI PLANT NAMED 'HFR18'

(50) Latin Name: ***Actinidia chinensis* Pl.**
Varietal Denomination: HFR18

(71) Applicant: Deyang Professional Academy of Kiwi Fruit, Sichuan Province (CN)

(72) Inventor: Guanyong Dong, Fangting Town (CN)

(73) Assignee: Deyang Professional Academy of Kiwi Fruit, Shifang County, Sichuan Province (CN)

( * ) Notice: Subject to any disclaimer, the term of this patent is extended or adjusted under 35 U.S.C. 154(b) by 0 days.

(21) Appl. No.: 14/999,909

(22) Filed: Jul. 18, 2016

(51) Int. Cl.
*A01H 5/08* (2006.01)

(52) U.S. Cl.
USPC ..... Plt./156

(58) Field of Classification Search
USPC ..... Plt./156
See application file for complete search history.

(56) References Cited

PUBLICATIONS

PLUTO Plant Variety Database Jun. 15, 2017 2 Pages.*
Printout of application information from Community Plant Variety Office (CPVO) website for corresponding CPVO application No. 2011/1085 filed Apr. 29, 2011 (1 page) (http://www.cpvoextranet.cpvo.europa.eu).
Printout of application information from Community Plant Variety Office (CPVO) website for corresponding CPVO application No. 2012/2809 filed Dec. 10, 2012 (1 page) (http://www.cpvoextranet.cpvo.europa.eu).
Chinese Plant Breeders' Rights Appl. No. 20130213.4 filed Mar. 20, 2013 (2 pgs.).

* cited by examiner

*Primary Examiner* — Annette Para
(74) *Attorney, Agent, or Firm* — Foley & Lardner LLP

(57) ABSTRACT

A new and distinct *Actinidia* plant named 'HFR18', particularly characterized by its strong growth habit, mid-April time to bloom and mid-September time to harvest, fruit size and shape, and pest resistance.

5 Drawing Sheets

Latin name of the genus and species of the plant claimed: *Actinidia chinensis* Pl.

Variety denomination: 'HFR18'.

BACKGROUND OF THE INVENTION

The present invention relates to a new and distinct cultivar of *Actinidia* plant, botanically known as *Actinidia chinensis* Pl. of the Actinidiaceae family, and hereinafter referred to by the variety denomination 'HFR18'.

The new *Actinidia* cultivar is a product of a controlled breeding and pollination program conducted by the inventor in Xia Yuan village, Shifang County, Sichuan Province, China. The objective of the breeding and pollination program was to develop a new *Actinidia* cultivar with redder fruit flesh color.

The new *Actinidia* cultivar originated from a controlled cross made by the inventor in April 2000 in Xia yuan village, Shifang County, Sichuan Province, China. The female or seed parent is the *Actinidia chinensis* Pl. cultivar 'Hongyang' (Registered; PVR in multiple regions). The male or pollen parent is the *Actinidia chinensis* Pl. cultivar 'SF0612M' (unpatented.)

Seeds were sown in February 2001 and 550 seedlings were then planted out in a field in a kiwifruit research station in Shifang county, Sichuan Province, China in February 2002. The seedlings first fruited in April 2005. A total of 2 female seedlings were propagated by graft in October 2007. The new *Actinidia* cultivar was selected by the inventor in a controlled environment in 2009 in Shifang county, Sichuan Province, China.

Asexual reproduction of the new *Actinidia* cultivar by grafting on rootstocks of *Actinidia deliciosa* C. F Liang was first performed in April 2010 in a kiwifruit research station in Shifang County, Sichuan Province, China and has demonstrated that the combination of characteristics as herein disclosed for the new cultivar are firmly fixed and retained through successive generations of asexual reproduction. The new cultivar reproduces true to type.

BRIEF DESCRIPTION OF THE INVENTION

The following traits have been repeatedly observed and are determined to be unique characteristics of 'HFR18' which in combination distinguish this *Actinidia* as a new and distinct cultivar:

1. Very strong growth habit. In soil of ph 5-6.5 and annual average temperature of 16-18° C., the claimed variety will fruit in the second year after grafting and can produce up to 20 t/ha of fruit by the fourth year of fruiting.
2. Flowering time and blooming period. Flowering time is in about mid-April in Sichuan Province, China and the blooming period is about 5 to 8 days.
3. Harvesting time. The harvesting time is in early-mid September in Sichuan Province, China.
4. Fruit Shape and Size. The general fruit shape is ovoid with a slightly depressed stylar end. The average fruit weight is 80 g and maximum fruit weight is 110 g;
5. Pest resistance. The claimed variety shows more resistance than the parent variety 'Hongyang'. There is some susceptibility to *Pseudaulacaspis pentagona*

(White Peach Scale); *Adoxophyes orana* Fisher (Summer fruit tortrix); *Acleris fimbriana* Thunberg (Yellow Tortrix Moth); and *Anomala corpulenta* Motsch. (Scarabaeidae).

In comparison to the female parent variety 'Hongyang' (Registered; PVR in multiple regions) and the male parent variety 'SF0612M' (unpatented), the claimed variety 'HFR18' differs primarily in the traits listed in Table 1.

TABLE 1

| Trait | New Cultivar 'HFR18' | Female Parent 'Hongyang' | Male Parent 'SF0612M' |
|---|---|---|---|
| Color of fruit skin | Yellow green and rough | Green and smooth | No fruit |
| Average fruit weight | 80 g | 54 g | No fruit |
| Fruit shape | ovoid | obovoid | No fruit |
| Color of inner pericarp (locules) | Red part larger | Red part smaller | No fruit |
| Fruit Core | No hollow | Hollow | No fruit |
| General shape of stylar end | Slightly depressed | Deeply depressed | No fruit |
| Plant resistance | More resistance | Less resistance | More resistance |

Of the many commercial varieties known to the present inventor(s), the most similar in comparison to the new *Actinidia* cultivar 'HFR18' is the female parent variety 'Hongyang' (Registered, PVR in multiple regions), in the following characteristics described in Table 2:

TABLE 2

| Characteristic | New Cultivar 'HFR18' | Comparison Cultivar 'Hongyang' |
|---|---|---|
| Color of fruit skin | Yellow green and rough | Green and smooth |
| Average fruit weight | 80 g | 54 g |
| Fruit shape | ovoid | obovoid |
| Color of inner pericarp (locules) | Red part larger | Red part smaller |
| Fruit Core | No hollow | hollow |
| General shape of stylar end | Slightly depressed | Deeply depressed |
| Plant resistance | More resistance | Less resistance |

BRIEF DESCRIPTION OF THE DRAWINGS

The accompanying photographs illustrate the overall appearance of the new *Actinidia* cultivar 'HFR18' showing the colors as true as is reasonably possible with colored reproductions of this type. Colors in the photographs may differ slightly from the color values cited in the detailed botanical description, which accurately describe the color of HFR18. Plants and plant parts of 'HFR18' shown in the photographs are from approximately 4 year old plants.

DETAILED BOTANICAL DESCRIPTION

Figure 1:
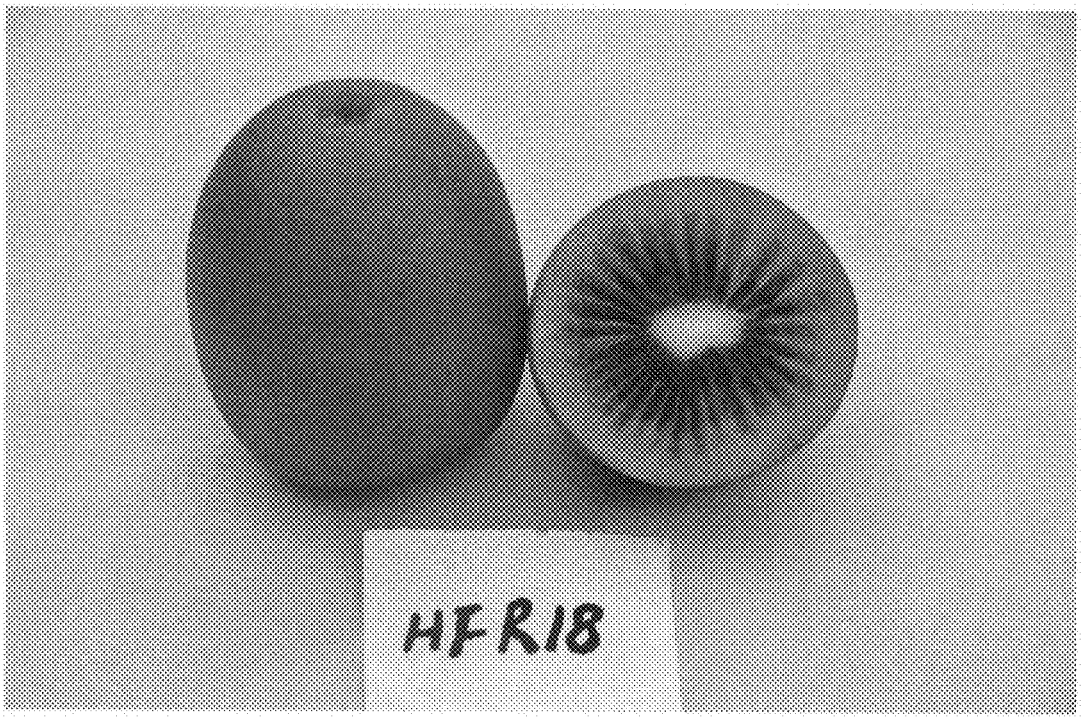
FIG. 1 shows a whole fruit and a cross section of a fruit of the claimed variety 'HFR18'.
Figure 2:
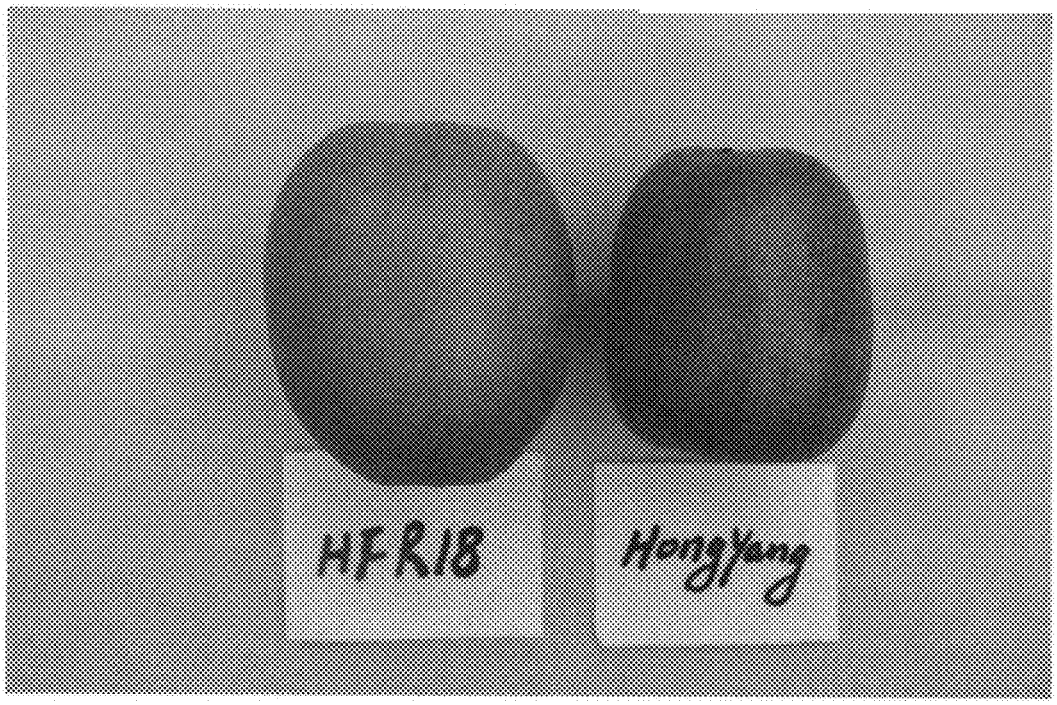
FIG. 2 shows a comparison between a whole fruit of the claimed variety 'HFR18' and the parent variety 'Hongyang'.
Figure 3:
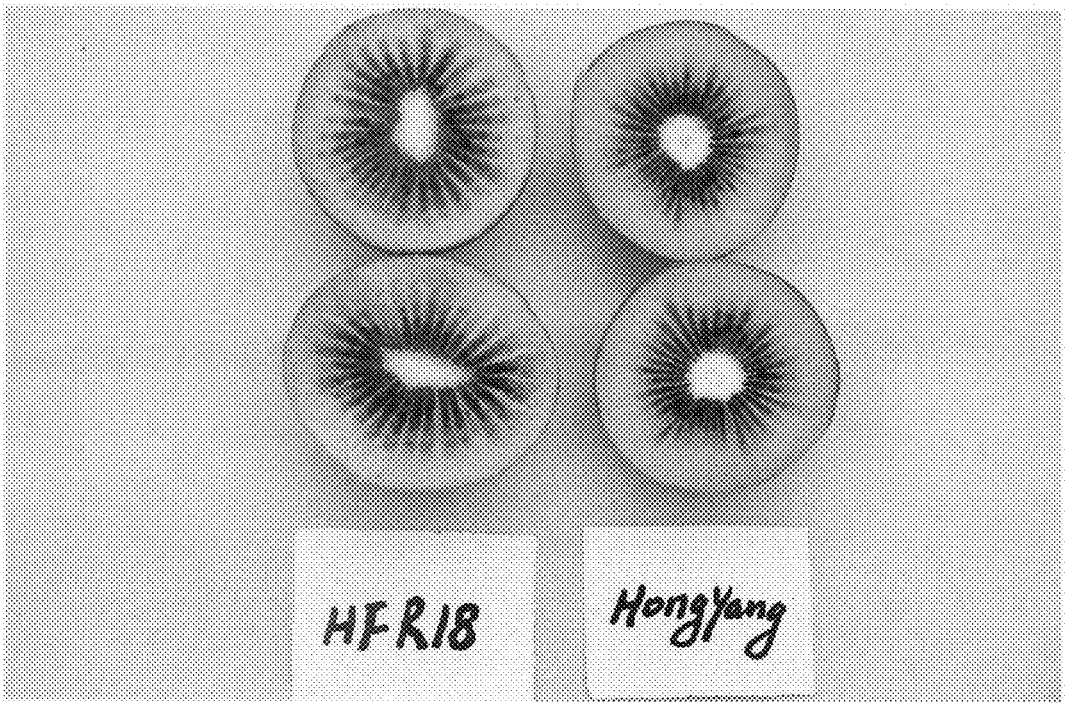
FIG. 3 shows a comparison between a cross-section of a fruit of the claimed variety 'HFR18' and of the parent variety 'Hongyang'.
Figure 4:
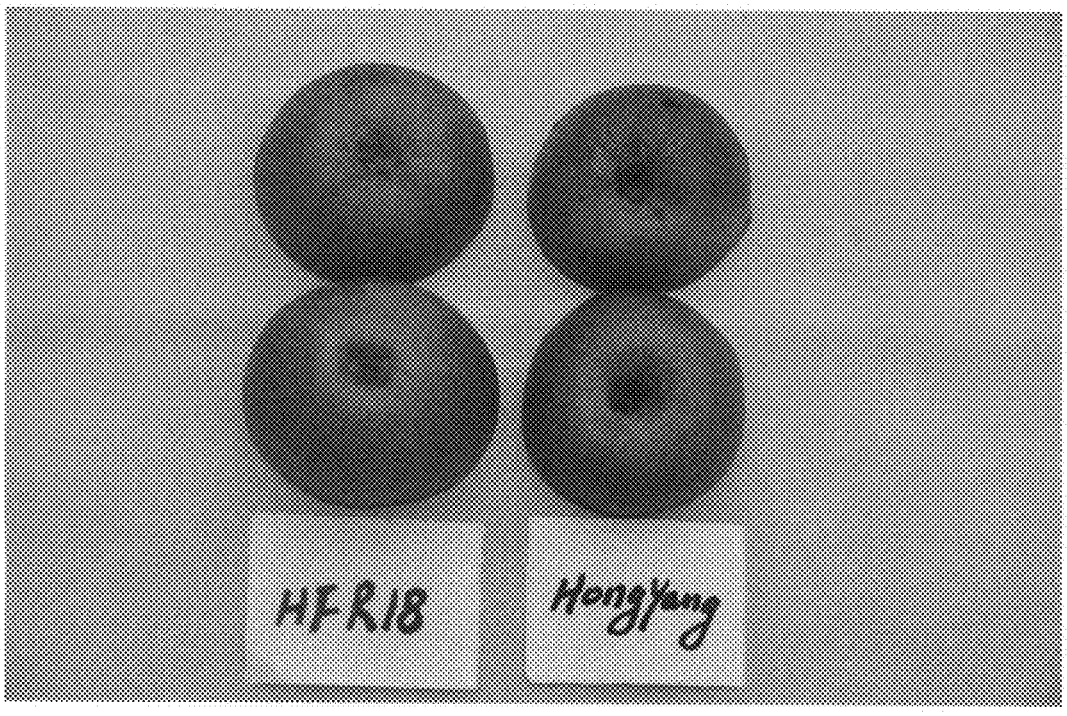
FIG. 4 is a different view of a comparison between a cross-section of a fruit of the claimed variety 'HFR18' and of the parent variety 'Hongyang', showing the differing stylar ends.
Figure 5:
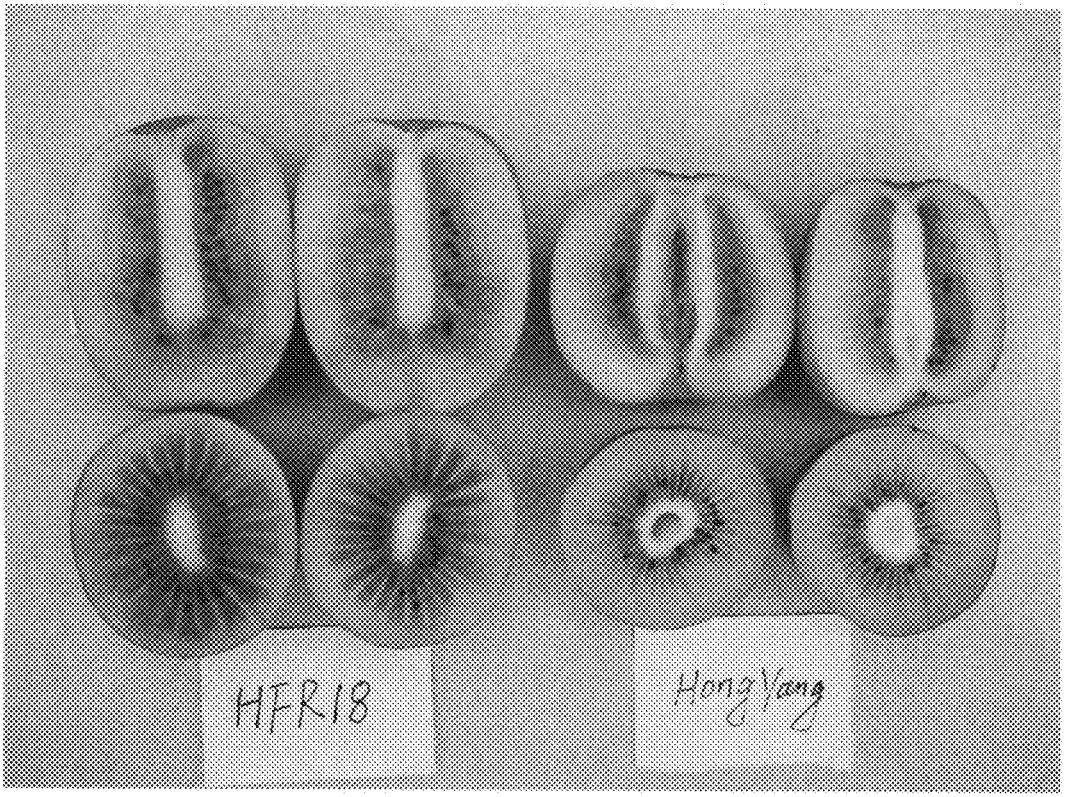
FIG. 5 shows a comparison between cross-sections of fruits of the claimed variety 'HFR18' and of the parent variety 'Hongyang'.

The new *Actinidia* cultivar 'HFR18' has not been observed under all possible environmental conditions. The phenotype of the new cultivar may vary with variations in environment such as temperature, light intensity, and day length without any change in the genotype of the *Actinidia*.

The aforementioned photographs, together with the following observations, measurements and values describe plants of 'HFR18' as grown outside in a kiwifruit research station in Shifang County, Sichuan Province, China under conditions which closely approximate those generally used in commercial practice.

Unless otherwise stated, the detailed botanical description includes observations, measurements and values based on 4 year old 'HFR18' plants grown in the field in a kiwifruit research station in Shifang County, Sichuan Province, China. Quantified measurements are expressed as an average of measurements taken from a number of plants of 'HFR18'. The measurements of any individual plant, or any group of plants, of the new cultivar may vary from the stated average.

Color references are made to The Royal Horticultural Society Colour Chart (R.H.S.) $4^{th}$ Edition, except where general colors of ordinary significance are used. Color values were taken under daylight conditions at approximately 10:00 AM in a kiwifruit research station in Shifang County, Sichuan Province, China.

All of the plants of 'HFR18', insofar as they have been observed, have been identical in all the characteristics described below.

Classification:

*Botanical.*—*Actinidia chinensis* Pl.

*Commercial.*—'HFR18'.

*Common.*—Kiwifruit, kiwi, Chinese gooseberry, Yangtao.

Parentage:

*Female or seed parent.*—*Actinidia chinensis* Pl. 'Hongyang' (Registered; PVR in multiple regions).

*Male or pollen parent.*—*Actinidia chinensis* Pl. 'SF0612M' (unpatented).

Propagation: Grafting onto rootstocks of *Actinidia deliciosa* C. F Liang.

Growing conditions:

*Light intensities.*—Full sunlight or slight shade.

*Temperature.*—During day, grown in range of 16° C. to 33° C., and during evening, grown in range of 10° C. to 28° C.

*Irrigation.*—Ample irrigation during growing season with good drainage is preferable.

*Fertilization.*—Plants prefer and thrive in soil rich in organic matter. Heavy nitrogen feeders during the first half of growing season.

*Ph.*—5.0 to 6.5.

*Growth regulators.*—No use.

*Pruning or trimming requirements.*—For best fruit production, "cane replacement" pruning during the winter season when plant is dormant. Pruned plants will remain more compact and bear larger fruit.

Plant:

*Sex expression*.—Female.

*Age*.—Observed plants were 4 years old.

*Vigor*.—Vigorous growth.

*Habit*.—Twining vine (liana), supported by fence system.

*Size at maturity* (*area covered by one plant*).—Length: Typical: About 3 m to 4 m. Observed: About 4 m to 5 m. Width: Typical: About 2 m to 3 m. Observed: About 3 m to 4 m. Height: Typical: About 2 m. Observed: About 2 m.

*Stem*.—Length: About 2 m to 4 m. Diameter: About 3 mm to 7 mm. Surface texture (upper/lower surface): smooth. Color (on sunny side; upper/lower surface): RHS 132B. Pith: present; pith type is hollow. Pubescence (upper/lower surface): downy and sparse.

*Young shoot*.—Length: Varies due to shape of plant; maximum of 2 m to 4 m; minimum of 30 cm to 50 cm. Diameter: About 5 mm to 25 mm. Surface texture (upper/lower surface): smooth. Pubescence (upper/lower surface): absent. Color: RHS 132D.

*Anthocyanin coloration of the growing tip*.—Strong.

*Mature laterals*.—Length: Varies due to shape of plant; maximum of 2 m to 3 m; minimum of 0.5 cm/m to 2.5 cm/m. Diameter: About 5 mm to 20 mm. Surface texture (upper/lower surface): smooth. Pubescence (upper/lower surface): absent. Color (upper/lower surface): RHS 22B.

*Lenticels*.—Length: About 0.2 mm to 0.5 mm. Width: About 0.2 mm to 0.5 mm. Color: RHS 155D. Density: few; about 1 to 2/cm$^2$.

*Buds*.—Shape: ellipsoid. Length: About 0.5 cm. Width: About 0.3 cm. Color: Apex, RHS 23C, and base, RHS 24A. Texture: deep. Pubescence: absent. Bud Support: Proximal Face: Perpendicular. Profile: straight. Size: small. Bud cover: absent.

*Leaf scar*.—Shallow.

*Leaves* (*matures*).—Arrangement and Aspect: touching each other. Size: Length: About 100 mm. Width: About 95 mm. Overall Shape: very broad ovate. Apex shape: acuminate. Base shape: touching each other. Distance between basal leaf lobes: About 50 mm. Pubescence: none. Puckering/blistering (upper/lower surface): weak. Glaucosity: Upper surface: absent. Lower surface: absent. Color: Upper surface: RHS 132D. Lower surface: RHS 132D. Venation: Type: feather shaped venation from central vein to the leaf edge. Color: RHS 132D.

*Leaf axil*.—Color: RHS 132B. Anthocyanin coloration: RHS 132B.

*Petiole*.—Length: About 77 mm. Diameter: About 2 mm. Texture: sparsely pubescent. Pubescence: very sparse to absent. Color: RHS 131B. Anthocyanin coloration (upper surface): RHS 131C.

*Stipule*.—None.

Inflorescence:

*Blooming time*.—Full bloom on or about April 10 in Sichuan Province, China.

*Blooming period*.—About 5 to 8 days.

*Fragrance*.—Typical of kiwifruit flower.

*Type*.—Cyme.

*Number of flowers per inflorescence*.—About 1-3.

*Inflorescence size*.—Diameter: About 31 mm. Depth: About 29 mm.

*Petals*.—Arrangement: overlapping. Mean number per flower: 5 to 6. Size: Length: About 31 mm. Width: About 29 mm. Length/width ratio: 1.1:1. Overall shape: broadly ovate. Apex shape: acute. Base shape: flat. Color (upper surface): RHS 155D. Color (lower surface): RHS 155D.

*Sepals*.—Arrangement: overlapping. Mean number per flower: 5 to 6. Size: Length: About 20 mm. Width: About 15 mm. Length/width ratio: 1.3:1. Overall shape: broadly ovate. Apex shape: acuminate. Base shape: flat. Color (upper surface): RHS 132B. Color (lower surface): RHS 132B.

*Pedicel*.—Length: About 35 mm. Diameter: About 2 mm. Texture: smooth. Color: RHS 131C.

Reproductive organs:

*Androecium*.—Stamen: Number: About 20 to 30. Length: About 1 mm. Color: RHS 19A. Anthers: Length: About 2 mm. Color: RHS 20A. Filaments: Length: About 3 mm. Color: RHS 20A. Pollen: Amount: scarce. Color: RHS 20A. Pollination Requirements: Almost all *Actinidia* species are dioecious, so female cultivars must be interplanted with male pollinizers to ensure fruit production on the female cultivar.

*Gynoecium*.—Pistils: Quantity: 31. Length: About 1 mm. Color: RHS 155D. Styles: Length: About 2 mm. Width: About 1.5 mm. Attitude: erect. Stigmas: Length: About 3 mm. Width: About 2 mm. Ovary: Shape: ovoid. Length: About 3 mm. Width: About 2 mm. Pubescence: none.

Fruit:

*Keeping quality*.—Fruits can be stored in cold temperature conditions for up to 12 weeks without losing firmness and juiciness. Fruits have a shelf life up to 12-16 weeks without losing firmness and juiciness.

*Number*.—About 100 per plant.

*Maturity when described*.—Harvest time is about 10 September in Sichuan Province, China. Fruit is ripe for eating at harvest.

*Firmness*.—About 1 kg/cm$^2$.

*Maturity period after full bloom*.—About 150 days after full bloom on April 10th.

*Type*.—Berry.

*Average fruit weight and size*.—Weight: About 80 g. Height: About 57 mm. Diameter (at widest point): About 45 mm. Diameter (at narrowest point): About 41 mm.

*Fruit shape*.—General shape: ovoid. Stylar end description: slightly depressed. Shoulder shape of stalk end: rounded. Cross-section shape at median: transverse elliptic.

*Skin*.—Firmness (at picking time): 3 to 4 kg/cm$^2$. Texture: smooth; lenticels are inconspicuous. Pubescence: none. Color: At harvest: RHS 131D. During ripening: RHS 131D. At maturity for consumption: RHS 131D.

*Flesh* (*at maturity for consumption*).—Texture: tender and juicy. Aroma: good. Sugar content (at picking time): 16.0 to 17.5° Brix. Acidity/Starch (at picking time) 1.5 to 1.8 g/lt.

*Dry Matter*.—18-19%.

*Acidity*.—1-1.8 g/kg.

*VC*.—>100 mg/100 g.

*Outer pericarp*.—RHS 1B.

*Inner pericarp* (*locules*).—Number (per fruit): About 28. Shape: oblong. Length: About 50 mm. Width: About 30 mm. Color: RHS 40A.

*Core*.—Shape and symmetry: oblong. Diameter (maximum): About 5 mm. Diameter (minimum): About 3 mm. Woody spike: absent. Color: RHS N155A.

Seeds:

*Number per fruit*.—About 1000-1500.

*Shape*.—Cylindrical.

*Length*.—About 1 mm.

*Width*.—About 0.5 mm.

*Texture*.—Striped, smooth.

*Color at maturity* (*in flesh*).—RHS 183A.

*Color at maturity* (*when dried*).—RHS 164A.

Cultivar use: Fresh market.

Disease/pest resistance: Pest resistance per square acre is stronger than the female parent 'Hongyang'.

Disease/pest susceptibility: Some susceptibility to *Pseudaulacaspis pentagona* (White Peach Scale); *Adoxophyes orana* Fisher (Summer fruit tortrix); *Acleris fimbriana* Thunberg (Yellow Tortrix Moth); and *Anomala corpulenta* Motsch. (Scarabaeidae).

Winter hardiness: Tolerant to temperatures down to 0° C. without observed damage to wood and buds of dormant *Actinidia* plants; but open flowers and young fruitlets are killed by exposure to −5° C., depending on the length of exposure.

Drought/heat tolerance: Tolerant to temperatures up to 35° C., growth is limited by drought periods without irrigation.

Events:

*Time of vegetative budbreak*.—Mid-February in Sichuan Province, China.

*Time of beginning of flowering*.—Mid-April in Sichuan Province, China.

*Time of maturity for harvest*.—Early to mid-September in Sichuan Province, China.

I claim:

1. A new and distinct *Actinidia chinensis* Pl. plant named 'HFR18', as illustrated and described herein.

* * * * *